United States Patent
Clark et al.

(10) Patent No.: US 10,758,637 B2
(45) Date of Patent: Sep. 1, 2020

(54) SYSTEMS, DEVICES, AND METHODS FOR GENERATING CHLORINE DIOXIDE

(71) Applicant: TBS Technologies, LLC, Holliston, MA (US)

(72) Inventors: Adrienne Clark, Waltham, MA (US); Paul Sabin, Needham, MA (US)

(73) Assignee: TBS Technologies, LLC, Holliston, MA (US)

( * ) Notice: Subject to any disclaimer, the term of this patent is extended or adjusted under 35 U.S.C. 154(b) by 297 days.

(21) Appl. No.: 15/690,817

(22) Filed: Aug. 30, 2017

(65) Prior Publication Data

US 2018/0064836 A1 Mar. 8, 2018

Related U.S. Application Data

(60) Provisional application No. 62/383,082, filed on Sep. 2, 2016.

(51) Int. Cl.
| | |
|---|---|
| *A61L 2/20* | (2006.01) |
| *C01B 32/50* | (2017.01) |
| *A61L 2/26* | (2006.01) |
| *B01J 7/02* | (2006.01) |
| *C01B 11/02* | (2006.01) |
| *C01B 3/08* | (2006.01) |

(52) U.S. Cl.
CPC .............. *A61L 2/20* (2013.01); *A61L 2/26* (2013.01); *B01J 7/02* (2013.01); *C01B 3/08* (2013.01); *C01B 11/024* (2013.01); *C01B 32/50* (2017.08); *Y02E 60/36* (2013.01)

(58) Field of Classification Search
CPC .............. A61L 2/20; A61L 2/26; C01B 11/024
See application file for complete search history.

(56) References Cited

U.S. PATENT DOCUMENTS

| | | | | |
|---|---|---|---|---|
| 2005/0031508 | A1* | 2/2005 | Abe .................... | B01D 19/0005 422/230 |
| 2005/0079123 | A1* | 4/2005 | Shuler .................. | A61K 33/40 423/477 |
| 2005/0244328 | A1* | 11/2005 | Schmitz ................ | A61L 2/20 423/477 |
| 2015/0273096 | A1* | 10/2015 | Takimoto .............. | A61L 2/20 422/187 |

* cited by examiner

*Primary Examiner* — Sean E Conley
(74) *Attorney, Agent, or Firm* — McCarter & English, LLP; Jonathan M. Sparks

(57) ABSTRACT

Methodologies, systems, and devices are disclosed for generating a chemical compound. A reaction chamber holds an amount of a precursor chemical, an activator chamber holds an amount of an activator chemical, and a quenching and neutralizer chamber holds an amount of quenching and neutralizing chemicals. A pump transfers the activator chemical from the activator chamber to the reaction chamber, where the activator chemical reacts with the precursor chemical to form the desired chemical compound. The desired chemical compound is allowed to exit the reaction chamber. Subsequently, the pump transfers the quenching and neutralizing chemicals from the quenching and neutralizer chamber to the reaction chamber, resulting in a quenched and neutralized solution.

13 Claims, 13 Drawing Sheets

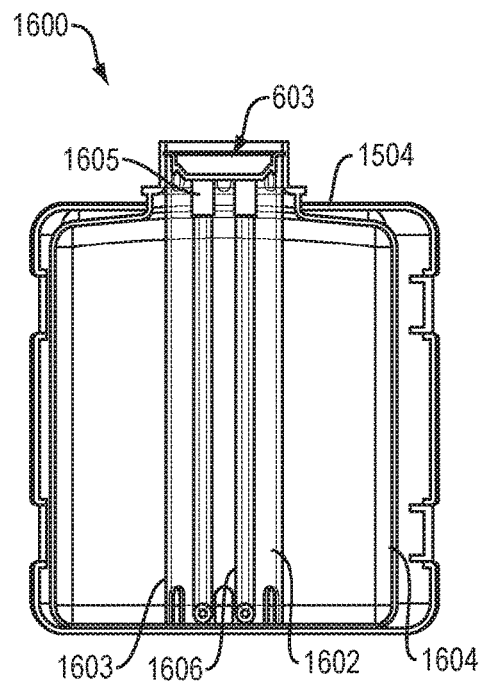
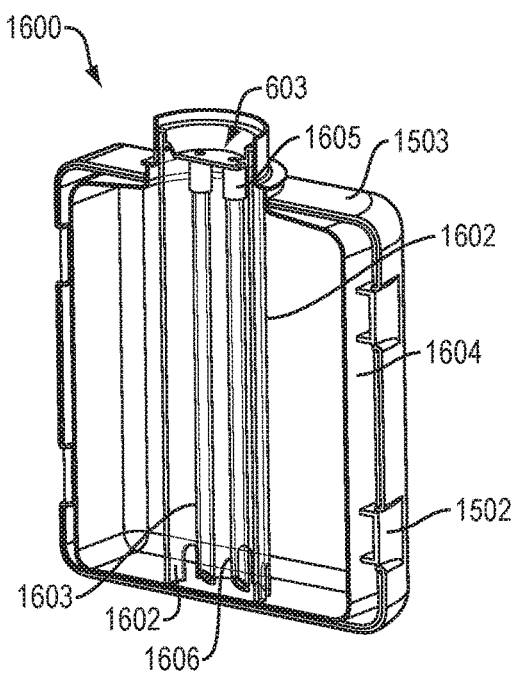
FIG. 17A     FIG. 17B
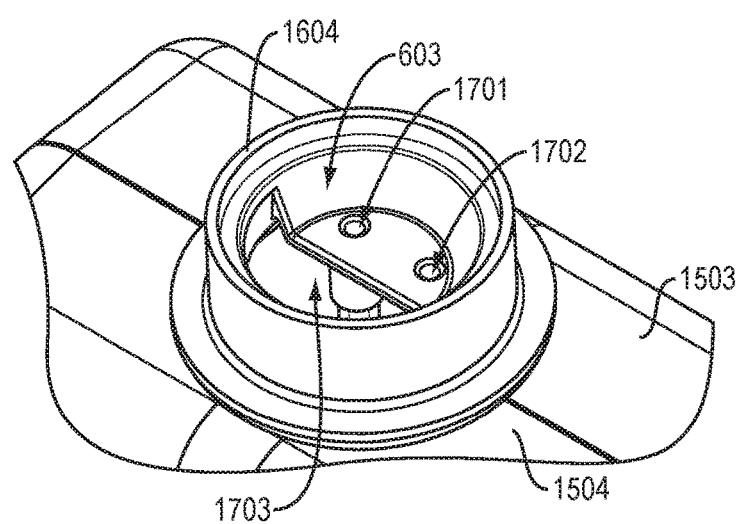
FIG. 18

SYSTEMS, DEVICES, AND METHODS FOR GENERATING CHLORINE DIOXIDE

RELATED APPLICATIONS

This application claims priority to U.S. Provisional Patent Application Ser. No. 62/383,082 entitled "SYSTEMS, DEVICES, AND METHODS FOR GENERATING CHLORINE DIOXIDE," filed on Sep. 2, 2016, the contents of which is hereby incorporated by reference in its entirety.

BACKGROUND OF THE TECHNOLOGY

Various types of chemical disinfectants and biocides can be used to reduce or eliminate bacteria, viruses, fungi, mold spores, algae, and protozoa. Chlorine dioxide ($ClO_2$) is one such chemical disinfectant.

SUMMARY

The present technology relates to generating chlorine dioxide for use in disinfecting spaces, surfaces, and equipment. In particular, the present disclosure relates to methodologies, systems and apparatuses for the generation of chlorine dioxide, e.g., aqueous chlorine dioxide or gaseous chlorine dioxide, for small and medium scale applications. The chlorine dioxide generators and disinfecting systems of the present disclosure can be used, for example, in a wide variety of applications, including in healthcare facilities, life science facilities, food facilities and other facilities.

In one embodiment, a system for generating a chemical compound is disclosed. The system includes a reaction chamber configured to hold a precursor chemical within its internal volume. A surface of the reaction chamber defines a reaction chamber opening providing fluid communication with the internal volume of the reaction chamber. The system also includes an activator chamber configured to hold an activator chemical within its internal volume. A surface of the activator chamber defines an activator chamber opening providing fluid communication with the internal volume of the activator chamber. The system also includes a neutralizer chamber configured to hold a quenching chemical and a neutralizer chemical within its internal volume. A surface of the neutralizer chamber defines a neutralizer chamber opening providing fluid communication with the internal volume of the neutralizer chamber. The system also includes a first fluid pathway disposed between the activator chamber opening and the reaction chamber opening and a second fluid pathway disposed between the neutralizer chamber opening and the reaction chamber opening. The system also includes a pump configured to selectively pump the activator chemical to the reaction chamber through the first fluid pathway and to pump the quenching and the neutralizer chemicals to the reaction chamber through the second fluid pathway.

In some embodiments, after the activator chemical is pumped into the reaction chamber, the neutralizer chemical can be directed to the activator chamber prior to being directed to the reaction chamber. This could neutralize any residual activator chemical left behind in the activator chamber or the fluid pathways before the neutralizer chemical is transferred to the reaction chamber.

In some embodiments, the precursor chemicals are precursor chemicals in an aqueous solution, the activator chemical is an activator chemical in an aqueous solution, and the quencher and neutralizer chemicals are in an aqueous solution used to quench and neutralize the reaction mixture in the reaction chamber. In some embodiments, the precursor chemical is a solution of $NaClO_2$ and the activator chemical is a solution of HCl, and the precursor chemical and the activator chemical react to form $ClO_2$ gas. In some embodiments, the reaction chamber opening is further configured to allow $ClO_2$ gas to exit from the reaction chamber. In some embodiments, the system also includes a reaction chamber insert configured to be received within the reaction chamber opening, an activator chamber insert configured to be received within the activator chamber opening, and a quenching and neutralizer chemical chamber insert configured to be received within the quencher and neutralizer chamber opening. In some embodiments, the first fluid pathway and the second fluid pathway form a microfluidic manifold with fluid pathways, and a portion of the manifold is configured to form a seal with the reaction chamber insert, the activator chamber insert, and the quencher and neutralizer chemical chamber insert. In some embodiments, a portion of the reaction chamber insert defines a vent configured to allow $ClO_2$ gas to exit from the reaction chamber. In some embodiments, the reaction chamber is a prefilled chemical cartridge containing a solution of $NaClO_2$. In some embodiments, the activator chamber is a prefilled chemical cartridge containing a solution of aqueous HCl. In some embodiments, the system also includes a fluid valve configured to allow the pump to selectively pump the activator chemical and the quencher and neutralizer chemical solution to the reaction chamber. In some embodiments, the valve can allow the pump to direct the quencher and neutralizer chemical solution to the activator chamber prior to being directed to the reaction chamber.

In another embodiment, a method for forming $ClO_2$ gas is disclosed. The method includes conveying, via a first pathway within a manifold, an aqueous solution of HCl to a reaction chamber, using a pump in fluid communication with an activator chamber containing the aqueous solution of HCl. The reaction chamber contains an aqueous solution of $NaClO_2$, and the method also includes forming $ClO_2$ gas within the reaction chamber. The method also includes emitting the $ClO_2$ gas from the reaction chamber.

In some embodiments, the method also includes conveying, via a second pathway within the manifold, a quenching and neutralizer aqueous solution to the reaction chamber, using the pump in fluid communication with a chamber containing the quenching and neutralizer solution. In some embodiments, the reaction chamber is a prefilled chemical cartridge containing an aqueous solution of $NaClO_2$. In some embodiments, the activator chamber is a prefilled chemical cartridge containing an aqueous solution of HCl. In some embodiments, the method also includes forming a seal between the manifold and the reaction chamber, the activator chamber, and the quenching and neutralizer chamber. In some embodiments, emitting the $ClO_2$ gas from the reaction chamber includes directing a flow of $ClO_2$ gas from the reaction chamber using a fan proximal to an outlet in the reaction chamber. In some embodiments, the method also includes operating a fluid valve to allow the pump to selectively pump the solution of HCl or the quenching and neutralizer aqueous solution to the reaction chamber.

In another embodiment, a disinfecting system is disclosed. The disinfecting system includes a prefilled reaction cartridge containing an aqueous solution of $NaClO_2$, a prefilled activator cartridge containing an aqueous solution of HCl, and a prefilled quenching and neutralizer chamber containing an aqueous quenching and neutralizer solution. The system also includes a manifold having a first pathway disposed between the activator cartridge and the reaction cartridge, and a second pathway disposed between the quenching and neutralizer cartridge and the reaction cartridge. The system also includes a pump in fluid communication with the activator cartridge and the quenching and neutralizer cartridge. The pump is configured to pump the solution of HCl to the reaction cartridge through the first pathway and to pump the quenching and neutralizer solution to the reaction cartridge through the second pathway. The aqueous solution of HCl and the aqueous solution of $NaClO_2$ react to form $ClO_2$ gas within the reaction cartridge. The system also includes a fan proximal to an outlet in the reaction cartridge and configured to direct a flow of $ClO_2$ gas from the reaction chamber.

In some embodiments, the system also includes a housing configured to receive the prefilled reaction cartridge, the prefilled activator cartridge, and the prefilled quenching and neutralizer cartridge. In some embodiments, the manifold is configured to form a seal with the prefilled reaction cartridge, the prefilled activator cartridge, and the prefilled quenching and neutralizer cartridge. In some embodiments, the system also includes a fluid valve configured to allow the pump to selectively pump the aqueous solution of HCl and the quenching and neutralizer aqueous solution to the reaction chamber.

Additional combinations and/or permutations of the above examples are envisioned as being within the scope of the present disclosure. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The foregoing and other features and advantages provided by the present disclosure will be more fully understood from the following description of exemplary embodiments when read together with the accompanying drawings, in which:

FIG. 17A illustrates a cross-sectional view of a reaction chamber housing and reaction chamber, according to embodiments of the present disclosure.

FIG. 17B illustrates a perspective cross-sectional view of the reaction chamber housing and reaction chamber of FIG. 17A.

FIG. 18 illustrates a perspective view of a reaction chamber insert piece within a reaction chamber, according to embodiments of the present disclosure.

DETAILED DESCRIPTION

Figure 1:
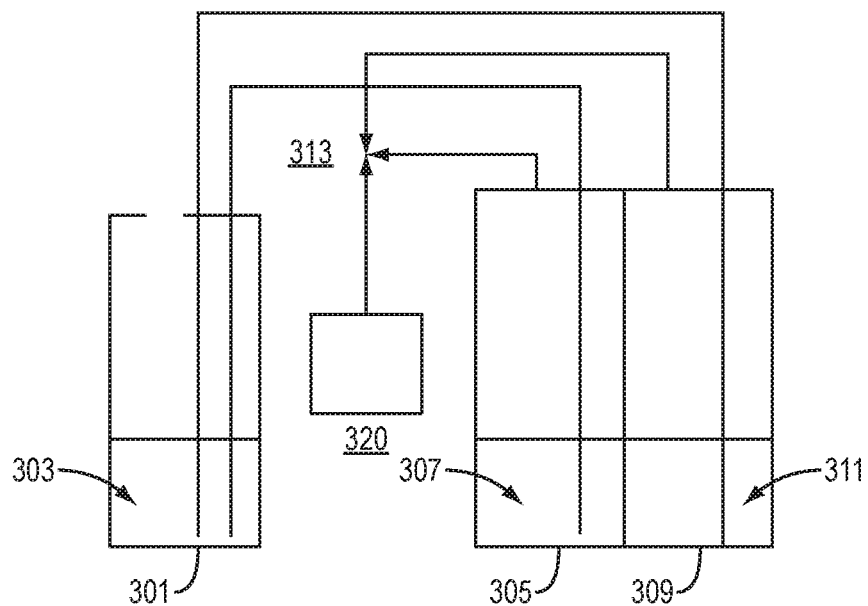
FIG. 1 is a block diagram of an exemplary system for generating a chemical compound, according to embodiments of the present disclosure.

Following below are more detailed descriptions of various concepts related to, and embodiments of, inventive methods, apparatus, and systems for generating $ClO_2$ and other chemical compounds. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

The present disclosure relates to systems, methods, and devices for generating chemical compounds, such as chlorine dioxide gas. Other examples include the creation of: carbon dioxide ($CO_2$) using sodium bicarbonate and hydrochloric acid ($NaHCO_3+HCl=>NaCl+CO_2+H_2O$); hydrogen sulfide ($H_2S$) (ferrous sulfide ($FeS$)$+2HCl=>H_2S$ (gas)$+FeCl_2$); and hydrogen gas ($2HCl+Zn=>ZnCl_2+H_2$ (gas)). In particular, embodiments of the present disclosure relate to generating $ClO_2$ gas for the disinfection of pharmaceutical equipment or facilities, food processing equipment or facilities, dental equipment or facilities, healthcare equipment or facilities, air handling equipment, filters, or for deodorizing purposes.

Chlorine dioxide inactivates microorganisms by oxidizing key components of membrane proteins that are vital to the membrane's structure and function, and hence to the microorganism's viability. It is generally understood that $ClO_2$ gas is a "true gas," meaning that it is a gas at standard temperature and pressure levels. Unlike vapors created by heating liquids until they vaporize, such as hydrogen peroxide vapor, $ClO_2$ does not condense at standard temperature and pressure levels and can provide a more thorough disinfection process. For example, a vapor may condense and provide less thorough penetration into microscopic crevices of an object being disinfected, which may lead to less effective and less predictable overall performance. Conventional $ClO_2$ generators can be suitable for large scale applications, but present challenges for smaller scale applications due to equipment cost, equipment size, length of cycle time, and complexity of use. Furthermore, conventional $ClO_2$ generators can present significant safety concerns due to the possibility of leaks in equipment, some of which use compressed chlorine gas ($Cl_2$) as a precursor chemical. Conventional $ClO_2$ equipment is designed for large applications but can be unwieldy and expensive when used for smaller applications, for example, when equipment capable of disinfecting a 70,000 ft³ space is used to disinfect a 40 ft³ biosafety cabinet. Various smaller scale applications such as biosafety cabinets, incubators, isolators, clean rooms, ambulances, food processing equipment, endoscopic equipment, dialysis machines, etc., can benefit from the use of $ClO_2$ as a disinfectant or sanitizing agent. In some embodiments, the $ClO_2$ generators disclosed herein can be under one cubic foot in size and can weigh under twelve pounds. The small size, easy portability, and simple operation of the $ClO_2$ generator disclosed herein provides a significant improvement in safety for the operators of the device. The invention may be placed inside the item to be disinfected, such as a biosafety cabinet, and any leakage from the device itself would be contained inside the item to be disinfected. The chemical containing chamber where the reaction takes place to produce the $ClO_2$ gas has a vent that allows $ClO_2$ gas to exit the chamber, thus preventing any unsafe build-up of $ClO_2$ gas, which is a concern with some conventional $ClO_2$ generators.

In some embodiments, a $ClO_2$ generator uses a plurality of chemical chambers that use micro-channel technology which allows for intercommunication between the plurality of chemical chambers. In one such embodiment, a $ClO_2$ generator includes a reaction chamber for generating an amount of $ClO_2$. The reaction chamber also has an outlet for discharging an amount of $ClO_2$ gas. The reaction chamber can include an aqueous solution of $NaClO_2$ (sodium chlorite). In some embodiments, the total amount and strength of the solution can be easily varied as determined by the requirements of a specific application. For example, a reaction chamber having different amounts or strengths of solution can be used depending on the amount of $ClO_2$ gas to be generated. The $ClO_2$ generator can also include an activator chamber for holding an aqueous solution of HCl (hydrochloric acid) which acts as the activator for the generation of $ClO_2$. In some embodiments, the total amount and strength of the activator solution can be determined by the requirements of a specific application. For example, an activator chamber having different amounts or strengths of activator solution can be used depending on the amount of $ClO_2$ gas to be generated. In some embodiments, other chemicals can be used as the activator chemical In various embodiments, the acid is selected from the group consisting of aqueous solutions of boric acid, tartaric acid, lactic acid, maleic acid, malic acid, glutaric acid, adipic acid, acetic acid, formic acid, oxalic acid, sulfamic acid, sulfuric acid, hydrochloric acid, phosphoric acid, phosphoric anhydride, sulfuric anhydride and citric acid.

The $ClO_2$ generator can also include a quenching and neutralizer chamber for holding a quenching and neutralizer aqueous solution, such as an aqueous solution of sodium sulfite and tri-sodium phosphate. Other examples of quenching chemicals can include, for example, sodium sulfite ($Na_2SO_3$), sodium bisulfite ($NaHSO_3$), sodium thiosulfate ($Na_2S_2O_3$), sodium metabisulfite ($Na_2S_2O_5$) and combinations thereof. Other examples of neutralizing or buffering chemical can include, for example, trisodiumphosphate ($Na_3PO_4$), disodiumphosphate ($Na_2HPO_4$) monosodiumphosphate ($NaH_2PO_4$), sodium hydroxide (NaOH), sodium carbonate ($Na_2CO_3$), sodium bicarbonate ($NaHCO_3$) and combinations thereof.

Quenching chemicals can react with any sodium chlorite in a solution that has not reacted to generate chlorine dioxide and can react with any chlorine dioxide gas still in solution, in both cases resulting in benign products. The solution which remains in the reaction chamber after the disinfection procedure is complete is acidic, and the neutralizer chemicals produce a solution with a pH acceptable for disposal, preferably with a pH between about 5.5 and 8.3.

In one embodiment, the $ClO_2$ generator can also include a polymeric manifold that has a series of fluid pathways that can provide fluid communication between the reaction chamber, the activator chamber, and the quenching and neutralizer chamber. The manifold can form a seal with the reaction chamber, the activator chamber, and the quenching and neutralizer chamber such that fluid can pass from the activator chamber to the reaction chamber and from the quenching and neutralizer chamber to the reaction chamber. In some embodiments, the polymeric manifold is included within or attached to a lid that can be closed and locked over the reaction chamber, the activator chamber, and the quenching and neutralizer chamber. A pump can generate air pressure to transfer the aqueous HCl solution from the activator chamber to the reaction chamber containing the aqueous $NaClO_2$ solution. With the introduction of the aqueous HCl solution to the aqueous $NaClO_2$ solution, the generation of $ClO_2$ begins. When the aqueous HCl solution has completely transferred, air from the pump continues to move through the microchannels or fluid pathways of the polymeric manifold and into the reaction chamber. This air agitates the reaction solution and aspirates the $ClO_2$ gas that is formed by the reaction of the $NaClO_2$ and HCl aqueous solutions. The $ClO_2$ gas can leave the reaction chamber through an open vent in the insert piece at the top of the reaction chamber. A fan located above the open vent in the insert piece of the reaction chamber can assist in the dispersal the gas into a target disinfection space, such as a biosafety cabinet or a clean room. This open vent eliminates the possibility of build-up of the $ClO_2$ concentration that would occur in the reaction chamber if the chamber was not vented, which is a significant safety feature.

In some embodiments, the present technology may incorporate a means to re-introduce the $ClO_2$ gas that has been generated to a solution and use the resultant $ClO_2$ solution for disinfection procedures without any of the typical undesirable reaction byproducts. This would provide an exceptionally pure $ClO_2$ solution with virtually no chlorites or chlorates as contaminants.

In some embodiments, a single outer housing can contain a plurality of the chemical containing chambers. In other embodiments, a physical scrubber or scrubber solution in another chemical chamber may be added to the system that could remove at least a portion of the $ClO_2$ gas from the generating solution or from the space being disinfected by passing the $ClO_2$ gas through the additional scrubbing unit or scrubbing chamber using a solution of sodium metabisulfite or other suitable chemical or chemicals. A physical scrubber containing carbon or other suitable material may also be used to remove $ClO_2$ gas, in some embodiments.

Exemplary embodiments are described below with reference to the drawings. One of ordinary skill in the art will recognize that exemplary embodiments are not limited to the illustrative embodiments, and, that components of exemplary systems, devices and methods are not limited to the illustrative embodiments described below.

FIG. 1 is a block diagram of an exemplary system for generating a chemical compound, according to embodiments of the present disclosure. A reaction chamber 301 holds an amount of a precursor chemical 303, and is in fluid communication with an activator chamber 309 and a neutralizer chamber 305. The activator chamber 309 can hold an activator chemical 311, and the quenching and neutralizer chamber 305 can hold quenching and neutralizer chemicals 307. A pump 320 is in fluid communication with the activator chamber 309 and the quenching and neutralizer chamber 305 via a valve 313, in this particular embodiment. The valve 313 can be a three-way valve, in some embodiments, and can be used to redirect air from the pump 320 through a microchannel or other fluid pathway to the activator chamber 309 or the quenching and neutralizer chamber 305.

Figure 2:
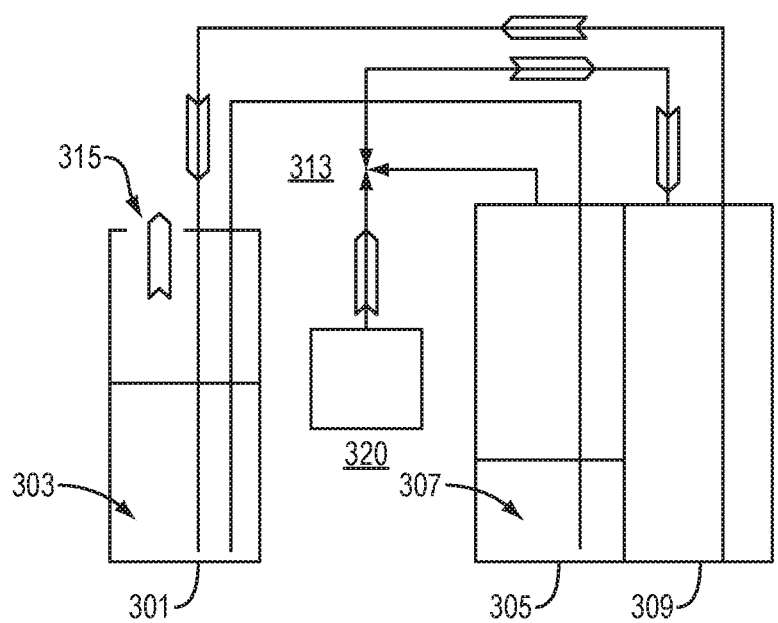
FIG. 2 is another block diagram of the exemplary system of FIG. 1.

FIG. 2 is another block diagram of the exemplary system of FIG. 1. In this particular embodiment, the 3-way fluid valve 313 is set such that the pump 320 is in fluid communication with the activator chamber 309. Once the pump 320 is activated, the activator chemical is transferred from the activator chamber 309 to the reaction chamber 301 and combines with the precursor chemical to generate the desired chemical compound 315. In some embodiments, the precursor chemical 303 is an aqueous solution of $NaClO_2$, the activator chemical 311 is an aqueous solution of HCl, and the desired chemical compound 315 produced is $ClO_2$ gas. In some embodiments, the activator chamber 309 and the quenching and neutralizer chamber 305 can be a single dual chemical chamber having separate interior volumes for holding the activator chemical 311 and the quenching and neutralizer chemicals 307, respectively.

Figure 3:
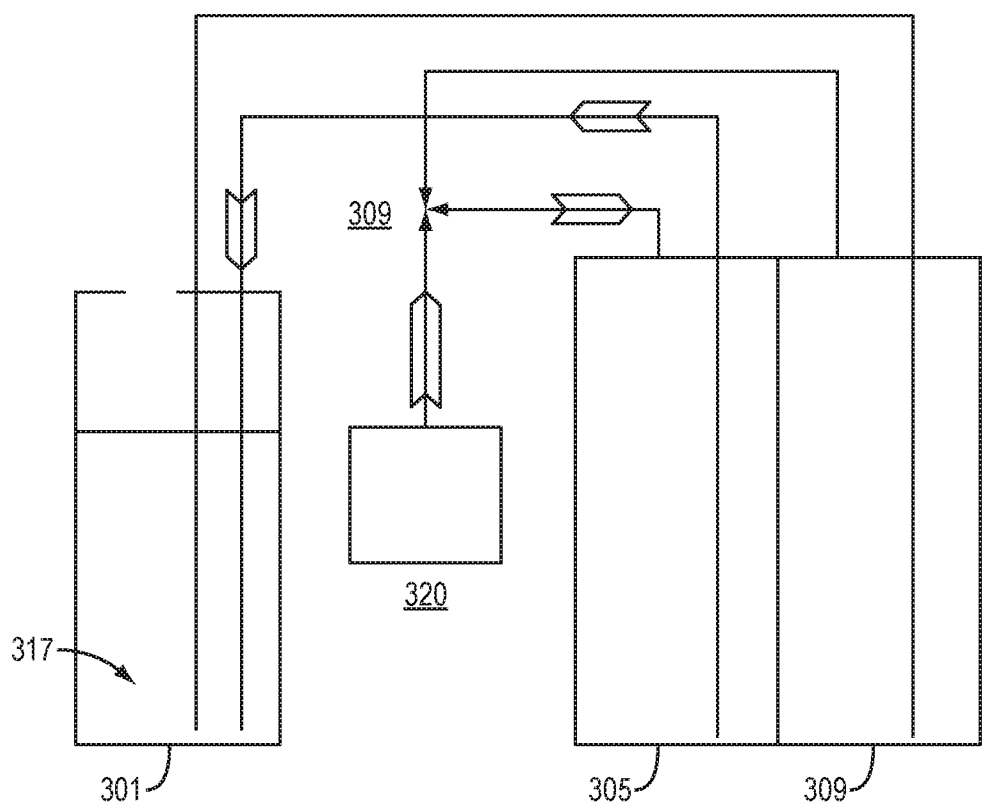
FIG. 3 is another block diagram of the exemplary system of FIGS. 1-2.

FIG. 3 is another block diagram of the exemplary system of FIGS. 1-2. After the activator chemical has been transferred to the reaction chamber 301, the 3-way fluid valve 313 is set such that the pump 320 is in fluid communication with the quenching and neutralizer chamber 305. Once the pump 320 is activated, the quenching and neutralizer chemicals are transferred from the quenching and neutralizer chamber 305 to the reaction chamber 301 and combines to form a neutralized solution 319. Within the reaction chamber, the quenching and neutralizer chemicals can consume any remaining unreacted $NaClO_2$ and quench any remaining $ClO_2$ gas. The resulting neutralized solution 317 can be acceptable for safe disposal and may have a pH between about 5.5 and 8.3.

Figure 4:
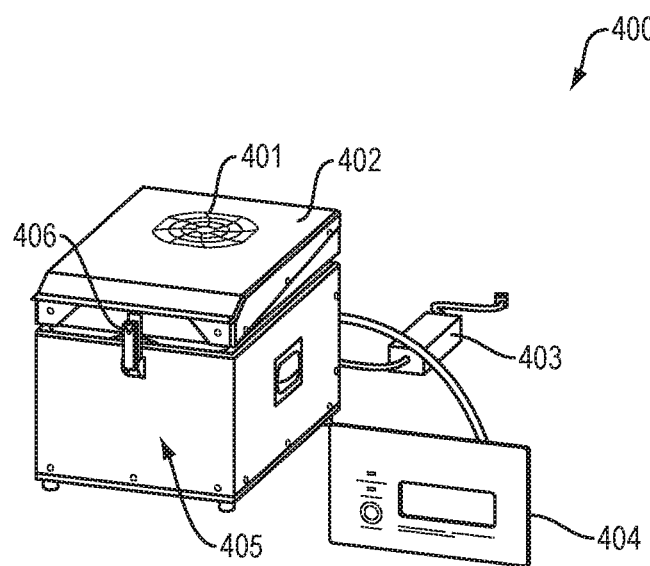
FIG. 4 illustrates an exemplary $ClO_2$ generator with a lid in the closed position, according to embodiments of the present disclosure.

FIG. 4 illustrates an exemplary $ClO_2$ generator 400 with a lid 402 in the closed position, according to embodiments of the present disclosure. In this particular embodiment, the $ClO_2$ generator 400 includes an AC/DC converter 403 that converts AC power to DC power. The housing 405 of the $ClO_2$ generator 400 can contain the chemical solutions described herein within their respective chambers (not shown). The $ClO_2$ generator 400 can be activated and controlled using a control box 404, and when $ClO_2$ gas is generated it can exit through an opening 401 in the lid 402. In some embodiments, a fan (not shown) can be built into the lid 402 at or near the opening 401 in order to disperse the $ClO_2$ gas. A latch 406 can be used to ensure a tight seal between the lid 402 and the housing 405 of the $ClO_2$ generator 400. In some embodiments, the control box 404 can include a control pad or other user interface that allows a user to control the amount of time the $ClO_2$ gas is dispersed and the amount of time allowed for quenching and neutralization, depending on the specific requirements of each application. In some embodiments, a $ClO_2$ measuring instrument may be integrated with the apparatus and used to control the rate at which the $ClO_2$ gas is released into the space to be treated, by controlling the rate at which air is moved through the reaction chamber, as well as measuring the concentration of the $ClO_2$ gas during the disinfection treatment cycle. In some embodiments, the components in the apparatus are designed to measure and regulate percent relative humidity (% RH) for specific applications such as the disinfection of bacterial spores. In some embodiments, the electric components in the apparatus are designed to operate under 12 VDC power. The DC power design allows for battery operation, battery back-up operation, or power from other DC power sources, making the light-weight portable apparatus suitable for field applications where a power grid may not be available with AC power.

In some embodiments, the $ClO_2$ generator 400 can have a fail-safe built into the programming of the control box 404 that prevents accidental activation of the $ClO_2$ generator 400. For example, an operator may be required to press a "start" button, release the start button, and then press the start button for an additional period of time when prompted by the control box 404 in order to activate the ClO$_2$ generator 400.

Figure 5:
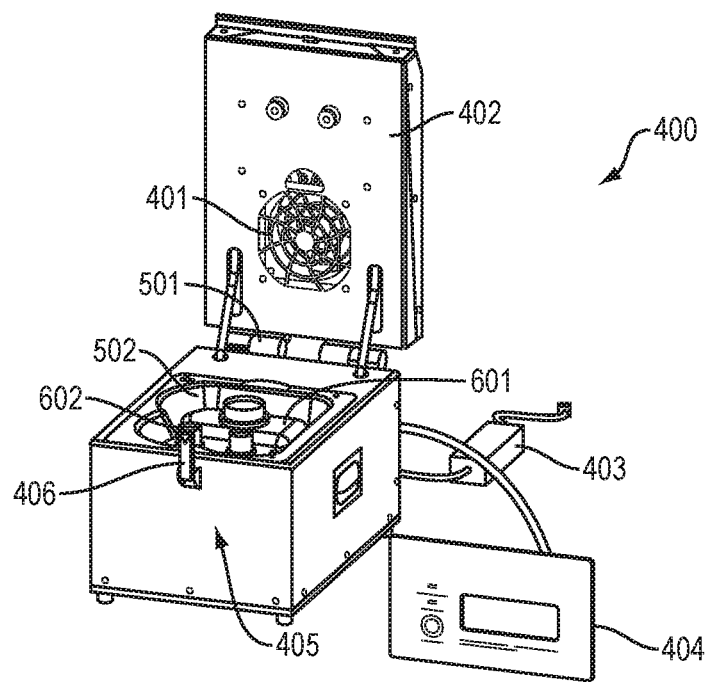
FIG. 5 illustrates the exemplary $ClO_2$ generator of FIG. 4 with the lid in an opened position.

FIG. 5 illustrates the exemplary ClO$_2$ generator 400 of FIG. 4 with the lid 402 in an opened position. In this particular embodiment, hinges 501 are used to allow the lid 402 to rotate from a closed position to an opened position. With the lid 402 in the opened position, a user can have access to the inside of the housing 405. In example embodiment, the interior of the housing 405 can receive a reaction chamber 601 and a dual chemical chamber 602, and an alignment piece 502 can hold the reaction chamber 601 and dual chemical chamber 602 in a specific orientation.

Figure 6:
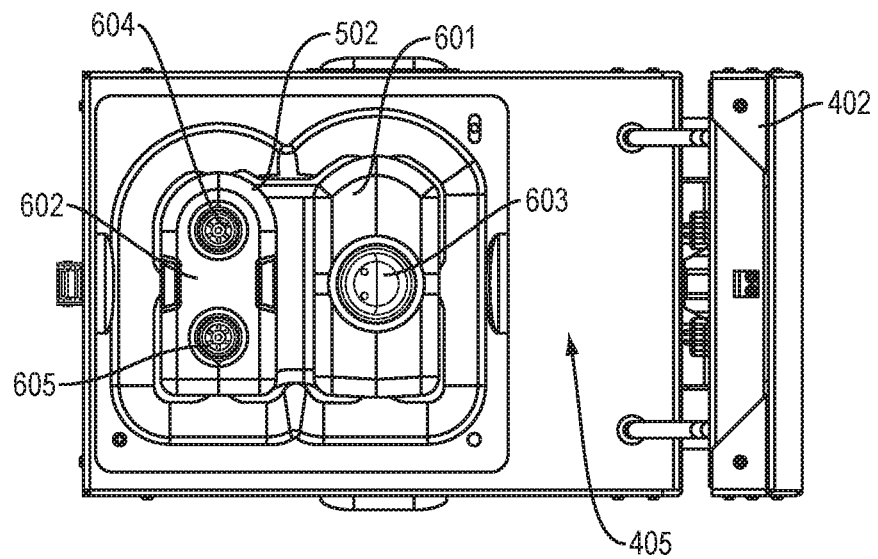
FIG. 6 illustrates an above-down view of the $ClO_2$ generator of FIGS. 4-5 with the lid in an opened position.

FIG. 6 illustrates an above-down view of the ClO$_2$ generator 400 of FIGS. 4-5 with the lid 402 in an opened position. In this example embodiment, the reaction chamber 601 is configured to hold an aqueous solution of NaClO$_2$, and the dual chemical chamber 602 is configured to have an activator chamber for holding an aqueous solution of HCl and a quenching and neutralizer chamber for holding an aqueous quenching and neutralizer solution. Once inserted in their respective positions within the housing 405, the reaction chamber 601 and the dual chemical chamber 602 are maintained in place using the alignment piece 502. The reaction chamber 601 has a reaction chamber insert piece 603, and the dual chemical chamber has two insert pieces 604, 605. Each of the insert pieces 603, 604, 605 can press-fit into openings in the reaction chamber 601 and the dual chemical chamber 602. The reaction chamber 601 and the dual chemical chamber 602 may be made from any material that is appropriate for the chemicals that they contain. The shape and size of the reaction chamber 601 and the dual chemical chamber 602 may be any shape and size that allows for the desired functionality. In some embodiments, the reaction chamber 601 and the dual chemical chamber 602 may be constructed using an injection molding process.

Figure 7:
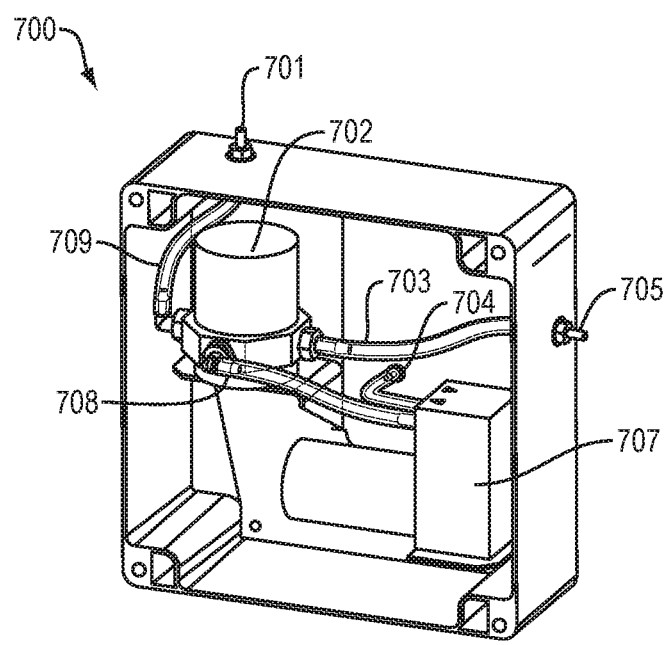
FIG. 7 illustrates an exemplary electrical box 700 for use in the $ClO_2$ generator 400 of FIGS. 4-6, according to embodiments of the present disclosure.

FIG. 7 illustrates an exemplary electrical box 700 for use in the ClO$_2$ generator 400 of FIGS. 4-6, according to embodiments of the present disclosure. The electrical box 700 can be located within the housing 405 of the ClO$_2$ generator 400. In some embodiments, the electrical box 700 is sealed to prevent ClO$_2$ gas from entering into the electrical box 700. In this example embodiment, the electrical box 700 includes a pump 707, a three-way valve 702, an inlet connection 704 to the pump 707, a pump outlet 708 from the pump 707 to the three-way valve 702, a first outlet 709 from the three-way valve 702, a first connector 701 that can connect the first outlet 709 to one of the chambers of the dual chemical chamber 602, a second outlet 703 from the three-way valve 702, and a second connector 705 that can connect the second outlet 703 to the other chamber of the dual chemical chamber 602. When the ClO$_2$ generator 400 is activated, the pump 707 provides air pressure through the pump outlet 708 to the three-way valve 702. Depending on the setting of the valve 702, the pump 707 will provide air pressure through either the first outlet 709 or the second outlet 703

Figure 8A:
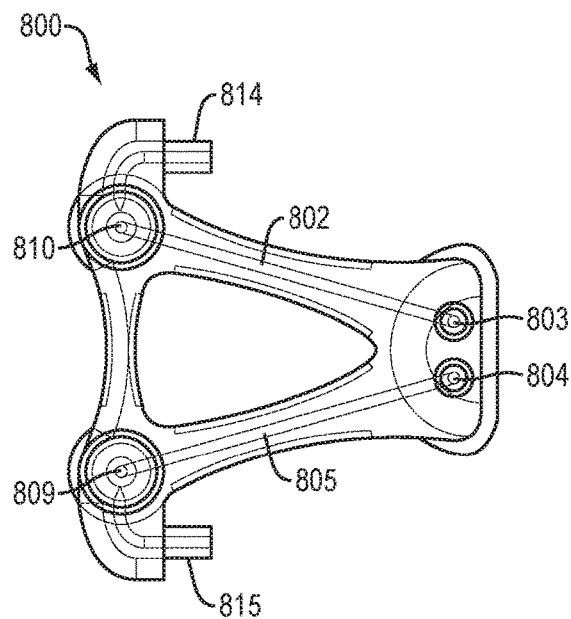
FIG. 8A is a transparent above-down view of an example polymeric manifold 800, according to embodiments of the present disclosure.
Figure 8B:
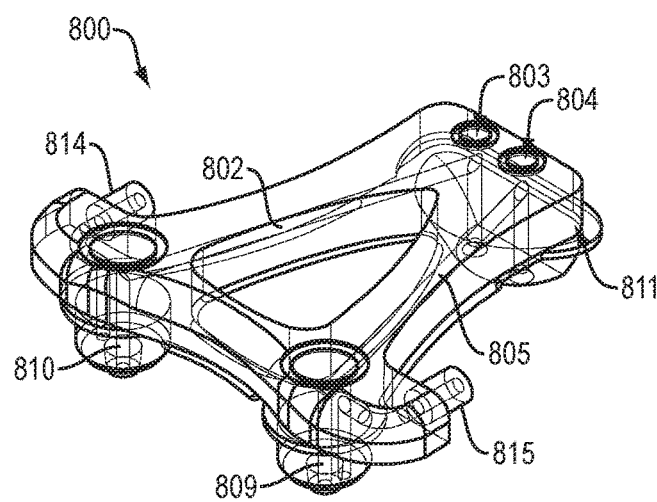
FIG. 8B is a transparent perspective view of the example polymeric manifold 800 of FIG. 8A.
Figure 8C:
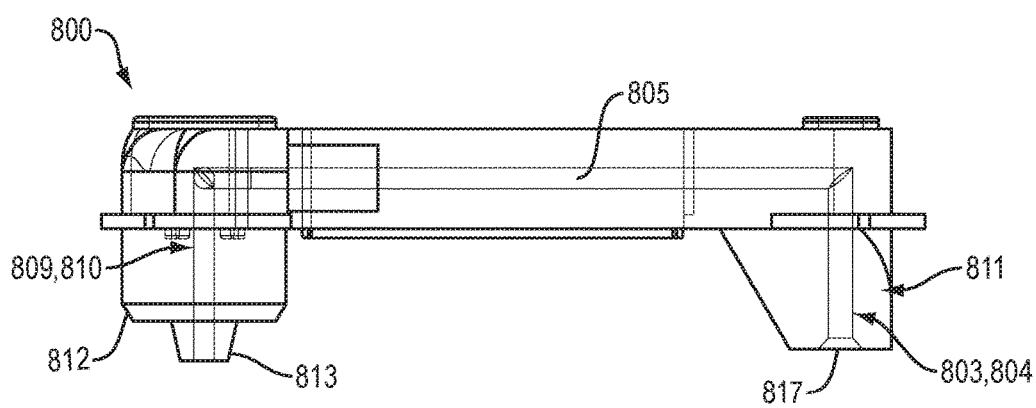
FIG. 8C is a transparent side view of the example polymeric manifold 800 of FIG. 8A.

FIGS. 8A-8C illustrate various views of an example polymeric manifold 800, according to embodiments of the present disclosure. FIG. 8A is a transparent above-down view of the polymeric manifold 800, FIG. 8B is a transparent perspective view of the polymeric manifold 800, and FIG. 8C is a transparent side view of the polymeric manifold 800. In this particular embodiment, the polymeric manifold 800 is configured to be located within or form a part of the lid 402 of the ClO$_2$ generator 400. The polymeric manifold has internal fluid pathways or microchannels that allow movement of air and liquids through the polymeric manifold. When the lid 402 is closed, the polymeric manifold forms a series of sealed fluid pathways between the reaction chamber 601 and the activator chamber and quenching and neutralizer chamber of the dual chemical chamber 602. The polymeric manifold 800 includes a first protrusion 809 and a second protrusion 810, each protrusion having a chamfered outlet 813 and a beveled sealing surface 812. The first protrusion 809 and the second protrusion 810 are configured to engage with the insert pieces 604, 605 of the dual chemical chamber 602. A third protrusion 811 in the polymeric manifold 800 has a first microchannel 804 and a second microchannel 803, each with an internal beveled surface 817 that is configured to engage with the reaction chamber insert piece 603 of the reaction chamber 601. The polymeric manifold 800 is in fluid communication with the pump 707 and receives air pressure through a first polymeric manifold inlet 815 and a second polymeric manifold inlet 814. The first microchannel 804 is configured to be in fluid communication with a first fluid pathway 805 between the first protrusion 809 and the third protrusion 811, and the second microchannel 803 is configured to be in fluid communication with a second microchannel pathway 802 between the second protrusion 810 and the third protrusion 811.

In one example embodiment, when the pump 707 is activated, air flows through the first polymeric manifold inlet 815 through the first protrusion 809 of the polymeric manifold 800 and through the insert piece 605 into the activator chamber of the dual chemical chamber 602. The air pressure in the activator chamber provides pressure to force the activator solution out of the activator chamber through the first fluid pathway 805 in the polymeric manifold 800 through the first microchannel 804 and into the reaction chamber 601, where the activator solution and the aqueous NaClO$_2$ solution mix, react, and produce ClO$_2$ gas which can escape through an opening or vent in the reaction chamber insert piece 603. In some embodiments, bubbling may be used to strip out all or a portion of the gas from the solution. In one example embodiment, after disinfection is complete, the three-way valve 702 can be switched such that air pressure from the pump 707 provides air pressure through the second polymeric manifold inlet 814 through the second protrusion 810 of the polymeric manifold 800 and through the insert piece 604 into the quenching and neutralizer chamber of the dual chemical chamber 602. The air pressure in the quenching and neutralizer chamber provides pressure to force the quenching and neutralizer solution out of the quenching and neutralizer chamber through the second microchannel pathway 802 in the polymeric manifold 800 through the second microchannel 803 and into the reaction chamber 601, where the quenching and neutralizer solution reacts to form a final neutralized solution. In some embodiments, bubbling may be used to aid in mixing the solution.

In some embodiments, there is a fail-safe feature inherent in the design of the ClO$_2$ generator 400 and polymeric manifold 800. For example, the ClO$_2$ generator 400 may be designed such that it will not transfer fluids from one chemical containing chamber to another if the seal between the polymeric manifold 800 and the chemical containing chambers is not sufficient. In the event of a misalignment of components or a failure to properly seal the ClO$_2$ generator 400, the device will not generate any ClO$_2$ gas.

In some embodiments, the pump 707 can also remove fluids from the microchannel pathways of the polymeric manifold 800, thus reducing the possibility of blockage within the polymeric manifold 800 due to the formation of chemical residues.

Figure 9:
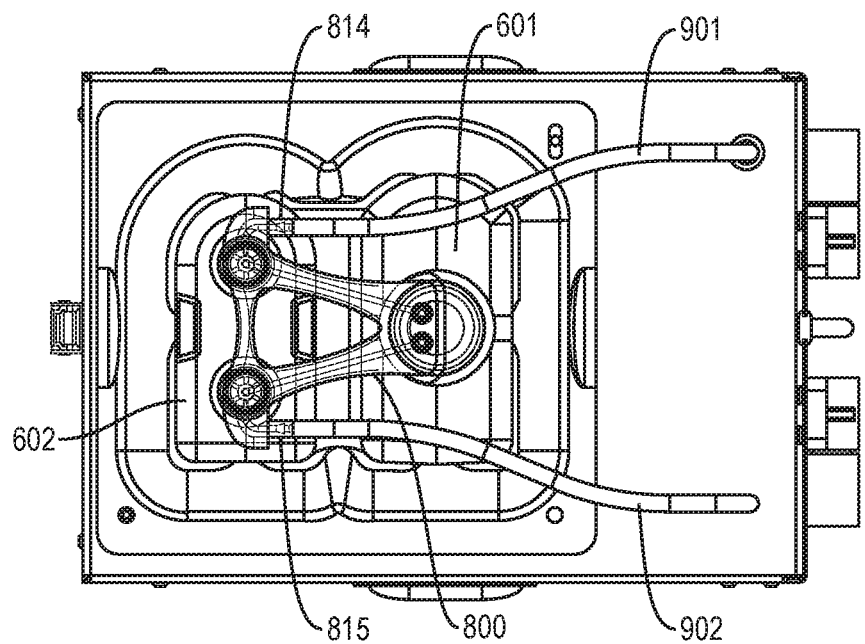
FIG. 9 illustrates an above-down view of a polymeric manifold placed on a reaction chamber and dual chemical chamber, according to embodiments of the present disclosure.

FIG. 9 illustrates an above-down view of the polymeric manifold 800 placed on the reaction chamber 601 and dual chemical chamber 602, according to embodiments of the present disclosure. In this example embodiment, the first polymeric manifold inlet 815 can communicate with the pump 707 through a first tube 902 that can connect with the first connector 701. Similarly, the second polymeric manifold inlet 814 can communicate with the pump 707 though a second tube 901 that can connect with the second connector 705.

Figure 10:
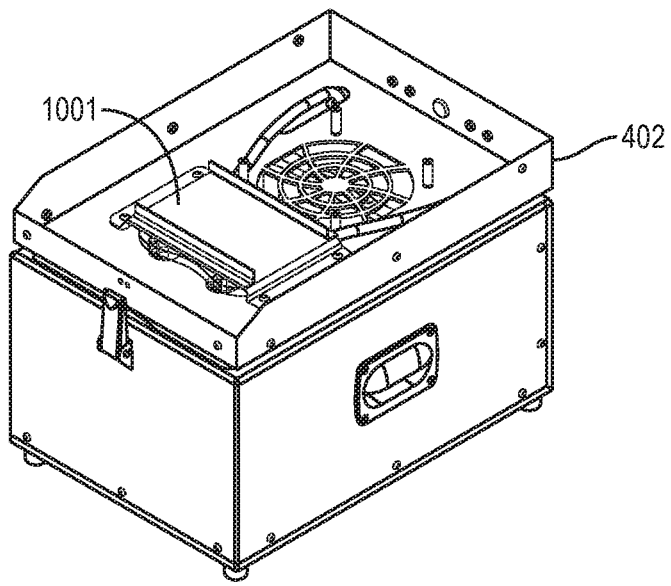
FIG. 10 shows an exemplary polymeric manifold mount within the lid of the $ClO_2$ generator, according to embodiments of the present disclosure.

FIG. 10 shows an exemplary polymeric manifold mount 1001 within the lid 402 of the $ClO_2$ generator 400, according to embodiments of the present disclosure. In this example embodiment, the polymeric manifold mount 1001 can hold the polymeric manifold 800 firmly in place and can be loosened to allow repositioning and adjustment of the polymeric manifold in order to assure correct alignment and proper sealing of the polymeric manifold 800 to the reaction chamber insert piece 603 and the dual chemical chamber insert pieces 604, 605.

Figure 11A:
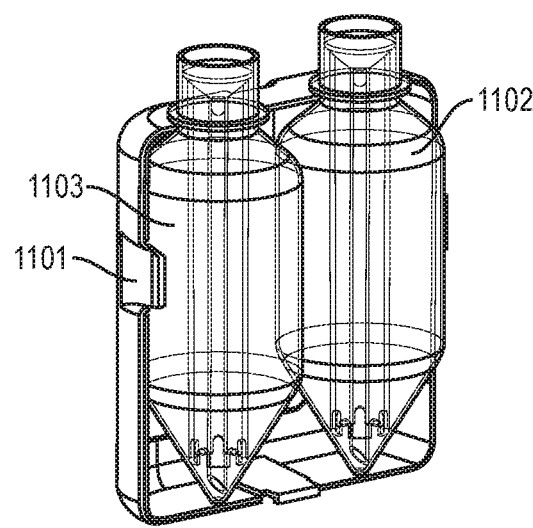
FIG. 11A shows an interior of a dual chemical chamber holding the activator chamber and the quenching and neutralizer chamber, according to embodiments of the present disclosure.
Figure 11B:
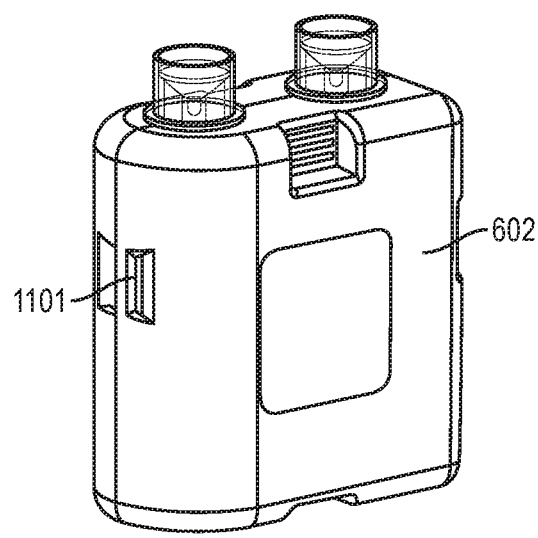
FIG. 11B shows an exterior of the dual chemical chamber of FIG. 11A, according to embodiments of the present disclosure.

FIGS. 11A-11B show details of the dual chemical chamber 602, according to embodiments of the present disclosure. FIG. 11A shows the interior of the dual chemical chamber 602 holding the activator chamber 1102 and the quenching and neutralizer chamber 1103. FIG. 11B shows the exterior of the dual chemical chamber 602 with a snap latch 1101 locked. The snap latch 1101 of the dual chemical chamber 602 allows two halves of the dual chemical chamber 602 to be closed tightly to apply pressure to the chambers. In this example embodiment, the bottom portion of the activator chamber 1102 and the quenching and neutralizer chamber 1103 is conical. However, it will be appreciated that other geometries can be used for the activator chamber 1102 or the quenching and neutralizer chamber 1103. In some embodiments, a cap or outlet portion of the activator chamber 1102 and the quenching and neutralizer chamber 1103 can be removed without movement of the chambers. In some embodiments, the activator chamber 1102 can be a prefilled cartridge containing an aqueous solution of HCl. In some embodiments, the quenching and neutralizer chamber 1103 can be a prefilled cartridge containing an aqueous quenching and neutralizer solution. Prefilled chemical containing cartridges provide for improved safety and consistency of operation, because there is greater assurance of correct chemical solution quantities and solution strengths than if some or all of the chemicals were mixed or diluted on-site. Prefilling the chemical containing cartridges also allows the use of deionized or distilled water for all the chemical solutions, thus eliminating the possibility of performance variations due to differences in available water quality at the site. This is of particular importance for use in field locations, as is the ability to use the invention with DC power supplies.

Figure 12:
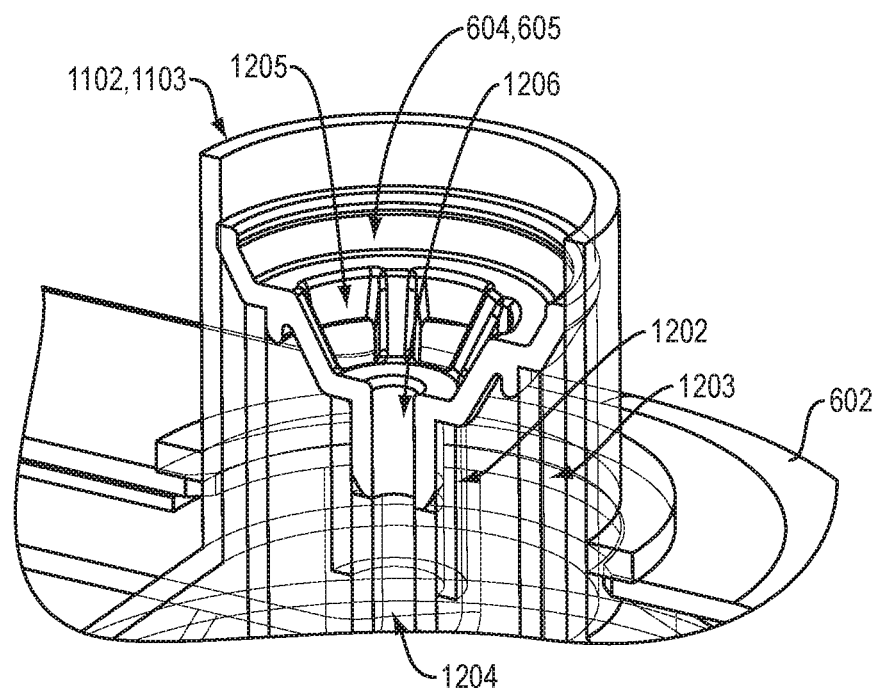
FIG. 12 illustrates a cross-sectional view of an exemplary insert assembly, according to embodiments of the present disclosure.

FIG. 12 illustrates a cross-sectional view of an exemplary insert assembly, according to embodiments of the present disclosure. In some embodiments, the insert assembly shown can be used for either of the activator chamber 1102 or the quenching and neutralizer chamber 1103 of the dual chemical chamber 602. The insert assembly includes an insert piece 604 or 605, which can be shaped and dimensioned to press-fit into an opening in the activator chamber 1102 or the quenching and neutralizer chamber 1103. In some embodiments, the insert piece 604, 605 can be made from acrylonitrile butadiene styrene (ABS), or other suitable materials. In this example embodiment, the insert piece 604, 605 ends in a tubular portion 1206 that fits into a tubular connector piece 1202, which in turn connects with a longer chemical chamber tube 1204 that extends at least partially within the activator chamber 1102 or the quenching and neutralizer chamber 1103. In some embodiments, the chemical chamber tube 1204 extends all the way to the bottom of the activator chamber 1102 or the quenching and neutralizer chamber 1103. The insert piece 604, 605 also includes one or more openings 1205 to allow passage of liquids or gas. An outer tubular member 1203 can at least partially surround the chemical chamber tube 1204 and can provide mechanical strength for the insert piece 604, 605 when the lid 402 closes and a portion of the polymeric manifold 800 applies a compression force on the insert piece 604, 605.

Figure 13A:
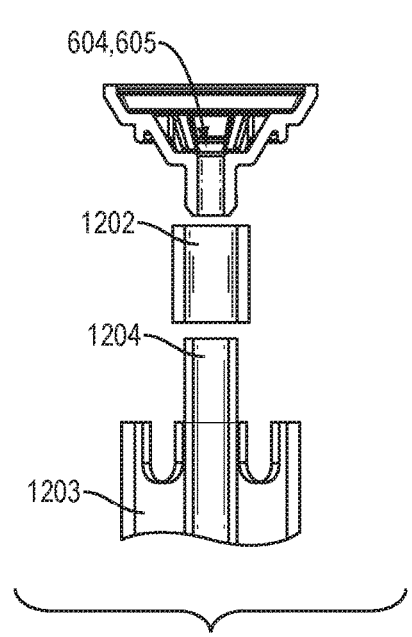
FIG. 13A illustrates an exploded view of an exemplary insert piece, tubular connector piece, chemical chamber tube, and outer tubular member, according to embodiments of the present disclosure.

FIG. 13A illustrates an exploded view of an exemplary insert piece 604, 605, tubular connector piece 1202, chemical chamber tube 1204, and outer tubular member 1203, according to embodiments of the present disclosure. As can be seen in this embodiment, the outer tubular member 1203 has crenellated ends.

Figure 13B:
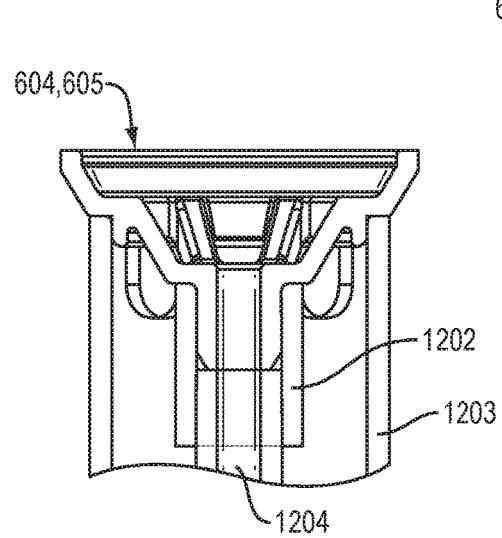
FIG. 13B illustrates a cross-sectional view of an exemplary insert piece, tubular connector piece, chemical chamber tube, and outer tubular member, according to embodiments of the present disclosure.

FIG. 13B illustrates a cross-sectional view of an exemplary insert piece 604, 605, tubular connector piece 1202, chemical chamber tube 1204, and outer tubular member 1203, according to embodiments of the present disclosure. In this example embodiment, the insert piece 604, 605, tubular connector piece 1202, chemical chamber tube 1204, and outer tubular member 1203 are assembled together.

Figure 13C:
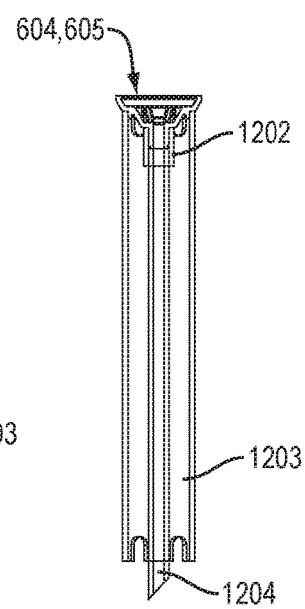
FIG. 13C illustrates another cross-sectional view of an exemplary insert piece, tubular connector piece, chemical chamber tube, and outer tubular member, according to embodiments of the present disclosure.

FIG. 13C illustrates another cross-sectional view of an exemplary insert piece 604, 605, tubular connector piece 1202, chemical chamber tube 1204, and outer tubular member 1203, according to embodiments of the present disclosure. In this example embodiment, both ends of the outer tubular member 1203 are crenellated, and the end portion of the chemical chamber tube 1204 has a diagonal cross section. The diagonal cross section can facilitate in removing a solution from either the activator chamber 1102 or the quenching and neutralizer chamber 1103.

Figure 14:
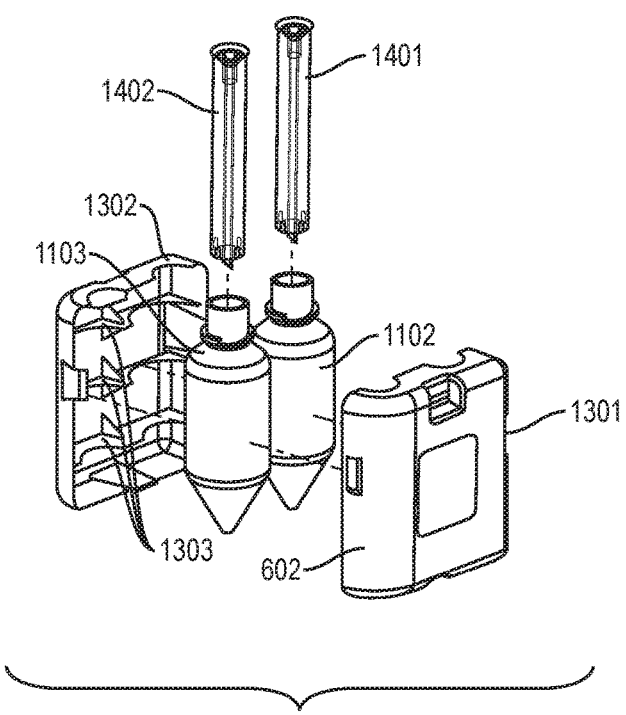
FIG. 14 illustrates an exploded view of a dual chemical chamber, i.e. the activator chamber, and the quenching and neutralizer chamber, and two insert assemblies, according to embodiments of the present disclosure.

FIG. 14 illustrates an exploded view of the dual chemical chamber 602, activator chamber 1102, quenching and neutralizer chamber 1103, and the insert assemblies 1401, 1402, according to embodiments of the present disclosure. The insert assemblies 1401, 1402 are assembled as discussed above in reference to FIG. 13C, and can fit within the activator chamber 1102 and the quenching and neutralizer chamber 1103, respectively. In this example embodiment, the dual chemical chamber 602 includes two housing pieces 1301, 1302 that can lock together in a closed position around the activator chamber 1102 and the quenching and neutralizer chamber 1103. The housing pieces 1301, 1302 also include internal ribs 1303 which can hold the activator chamber 1102 and the quenching and neutralizer chamber 1103 in place when the housing pieces 1301, 1302 are in the closed position.

Figure 15A:
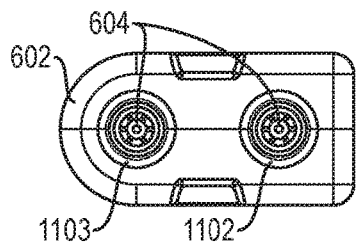
FIG. 15A illustrates a top view of a dual chemical chamber in the closed position, according to embodiments of the present disclosure.
Figure 15B:
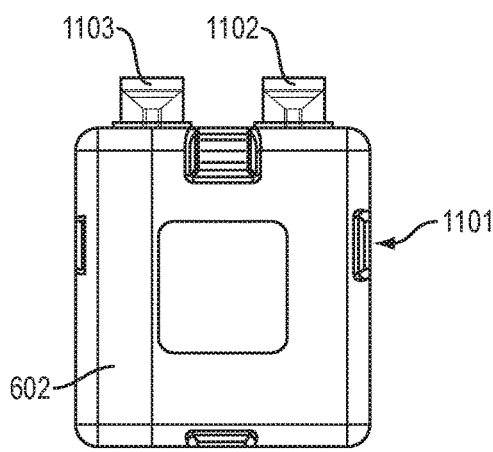
FIG. 15B illustrates a front view of the dual chemical chamber of FIG. 15A.
Figure 15C:
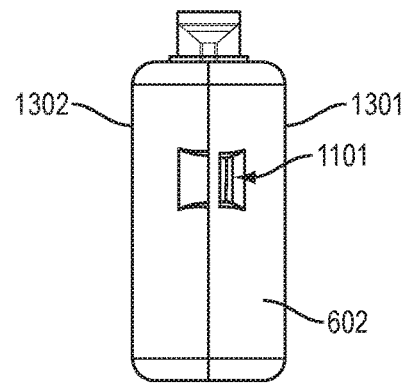
FIG. 15C illustrates a side view of the dual chemical chamber of FIGS. 15A-15B.

FIGS. 15A-15C illustrate various views of the dual chemical chamber 602, according to embodiments of the present disclosure. FIG. 15A illustrates a top view of the dual chemical chamber 602 in the closed position. FIG. 15B illustrates a front view of the dual chemical chamber 602 in the closed position. FIG. 15C illustrates a side view of the dual chemical chamber 602 in the closed position. In the front view and side view, the snap latch 1101 is in the locked position. The top portion of the activator chamber 1102 and the neutralizer chamber 1103 can be seen extending outside the two housing pieces 1301, 1302 of the dual chemical chamber 602.

Figure 16A:
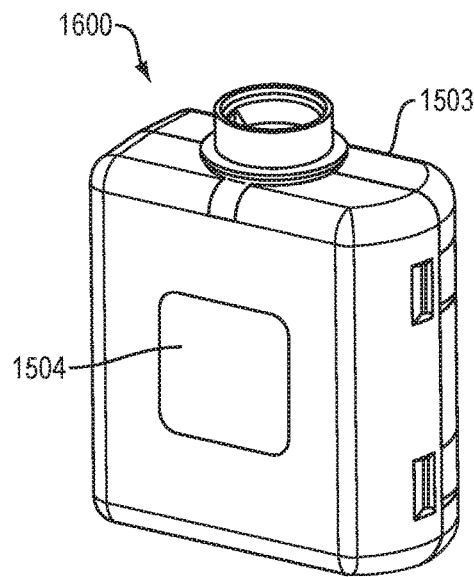
FIG. 16A illustrates a front perspective view of a reaction chamber housing, according to embodiments of the present disclosure.
Figure 16B:
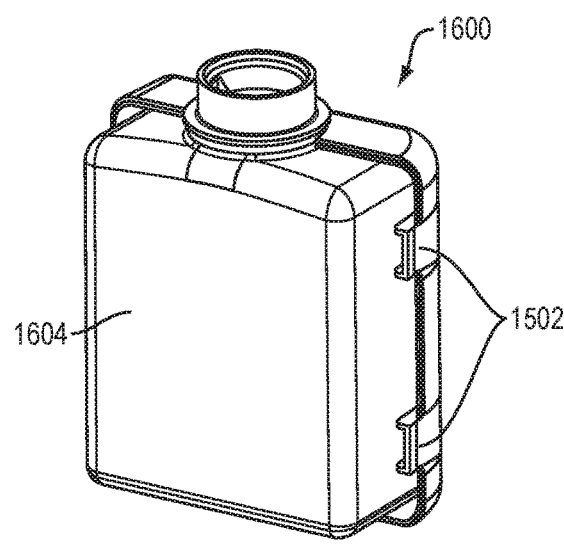
FIG. 16B illustrates a rear perspective view of a reaction chamber within the reaction chamber housing of FIG. 16A.

FIG. 16A illustrates a front perspective view of a reaction chamber housing 1600, according to embodiments of the present disclosure. FIG. 16B illustrates a rear perspective view of a reaction chamber 1604 within the reaction chamber housing 1600 of FIG. 16A. In this particular embodiment, the reaction chamber housing 1600 includes two housing pieces 1503, 1504 that can be closed and locked with a pair of latches 1502.

FIG. 17A illustrates a cross-sectional view of a reaction chamber housing 1600 and reaction chamber 1604, according to embodiments of the present disclosure. FIG. 17B illustrates a perspective cross-sectional view of the reaction chamber housing 1600 and reaction chamber 1604 of FIG. 17A. The reaction chamber housing 1600 includes two housing pieces 1503, 1504 that can fit together around the reaction chamber 1604. In this example embodiment, a reaction chamber insert piece 603 is configured to engage with two tubular connectors 1605, which in turn engage with a first reaction chamber tube 1606 and a second reaction chamber tube 1603 that extend at least partially within the reaction chamber 1604. An outer tubular piece 1602 at least partially surrounds each of the reaction chamber tubes 1603, 1606 and includes crenellations at each end.

FIG. 18 illustrates a perspective view of a reaction chamber insert piece 603 within a reaction chamber 1604, according to embodiments of the present disclosure. As discussed above, the reaction chamber 1604 can have two housing pieces 1503, 1504, and the reaction chamber insert piece 603 can be press-fit within the reaction chamber 1604. The reaction chamber insert piece 603 also includes a first opening 1702 and a second opening 1701 to allow inflow from the activator chamber and the quenching and neutralizer chamber, respectively. The first opening 1702 can mate with the beveled surface 817 of the first microchannel 804 of the polymeric manifold 800, and the second opening 1701 can mate with the beveled surface 817 of the second microchannel 803 of the polymeric manifold 800. The reaction chamber insert piece 603 also includes an opening or vent 1703 that allows for exit of $ClO_2$ gas generated within the reaction chamber. When the pump 707 is energized, the aqueous activator solution is transferred through the first opening 1702 of the reaction chamber insert piece 603 and into the reaction chamber 1604 through the first reaction chamber tube 1606. Subsequently, the quenching and neutralizer solution can be transferred through the second opening 1701 of the reaction chamber insert piece 603 and into the reaction chamber 1604 through the second reaction chamber tube 1603. In some embodiments, the reaction chamber 1604 can be a prefilled cartridge containing an aqueous solution of $NaClO_2$.

Figure 19:
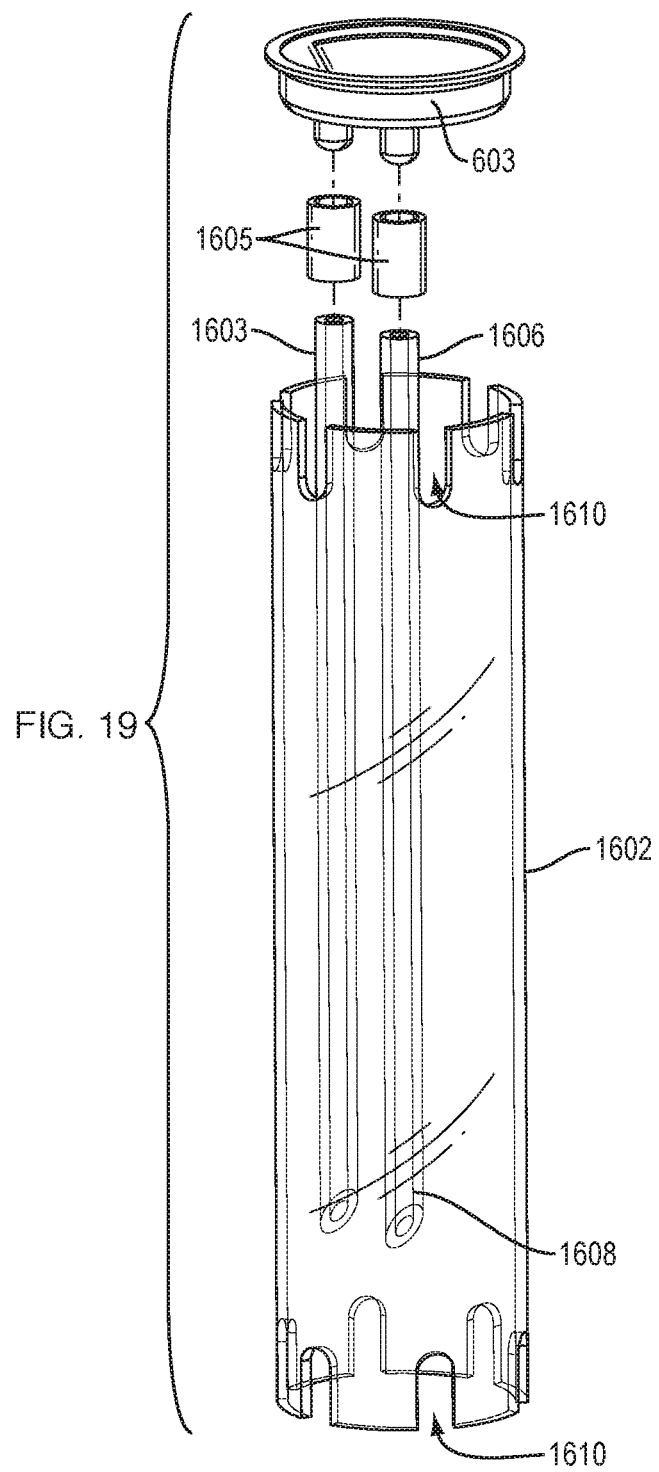
FIG. 19 illustrates an exploded view of a reaction chamber insert assembly, according to embodiments of the present disclosure.

FIG. 19 illustrates an exploded view of a reaction chamber assembly, according to embodiments of the present disclosure. In this example embodiment, the reaction chamber assembly includes the reaction chamber insert 603, the two tubular connectors 1605, the first reaction chamber tube 1606, the second reaction chamber tube 1603, and the outer tubular piece 1602. Each of the first reaction chamber tube 1606 and the second reaction chamber tube 1603 have a diagonal cross section at their ends 1608, and the outer tubular piece 1602 has crenellations at both ends 1610.

Figure 20:
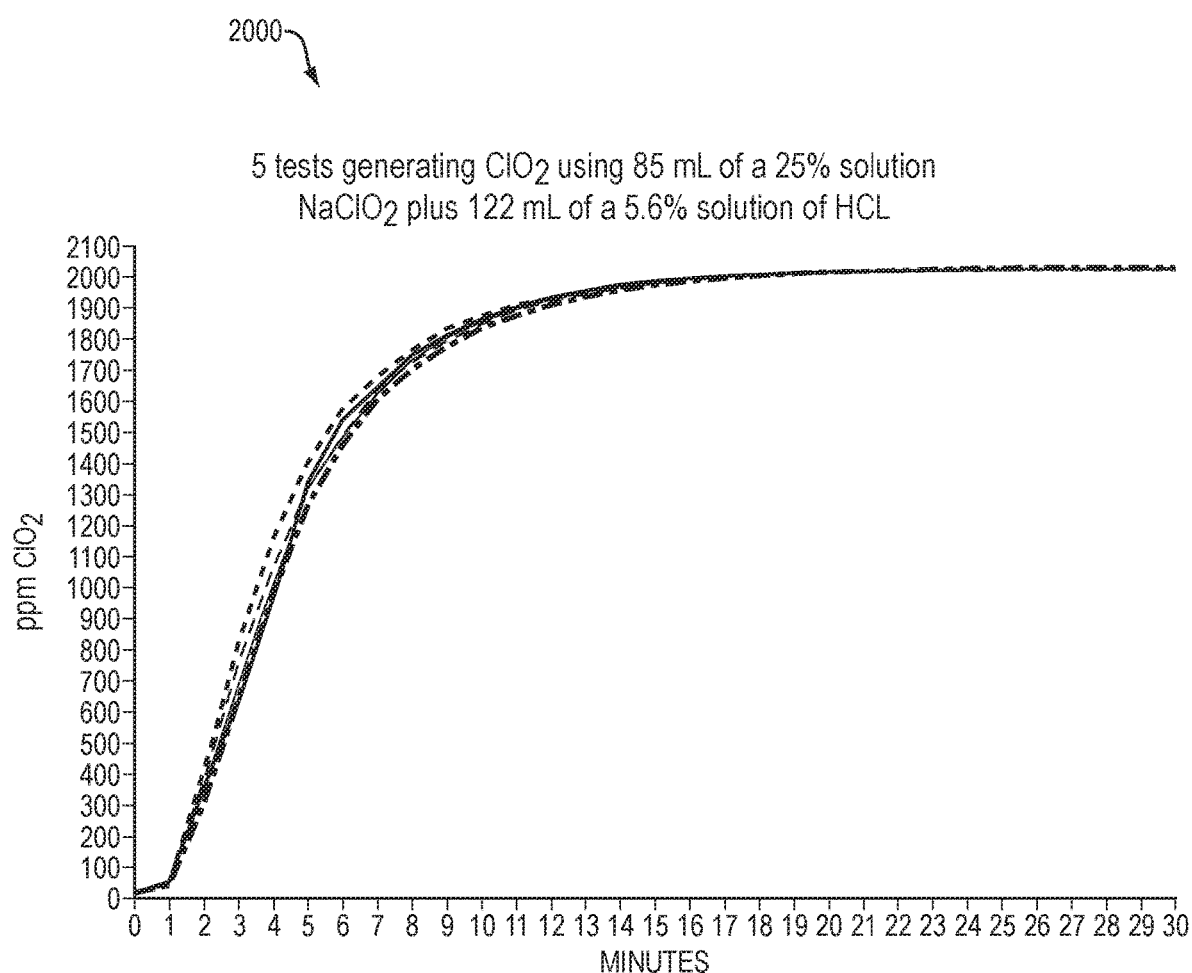
FIG. 20 shows a graph of the $ClO_2$ gas concentration in parts per million (ppm) from five test procedures of an example $ClO_2$ generator test, according to an embodiment of the present disclosure.

Experiments were conducted using the techniques described herein in test chamber constructed of PVC material having an internal volume of approximately sixty cubic feet. These experiments used 85 mL of a 25% $NaClO_2$ aqueous solution and 122 mL of a 5.6% aqueous solution of HCl. FIG. 20 shows a graph 2000 of the $ClO_2$ gas concentration in parts per million (ppm) over time from five test procedures of an example $ClO_2$ generator, according to embodiments of the present disclosure. In these example experiments, a concentration of over 1,000 ppm was achieved in approximately 4 minutes. Distilled water was used to make the chemical solutions. The calculated amount of $ClO_2$ produced was about 0.17 grams per cubic foot of volume. This satisfies the requirements of the National Science Foundation International Standard/American National Standard (NSF/ANSI) chlorine dioxide disinfection method for the disinfection of biosafety cabinets.

Figure 21:
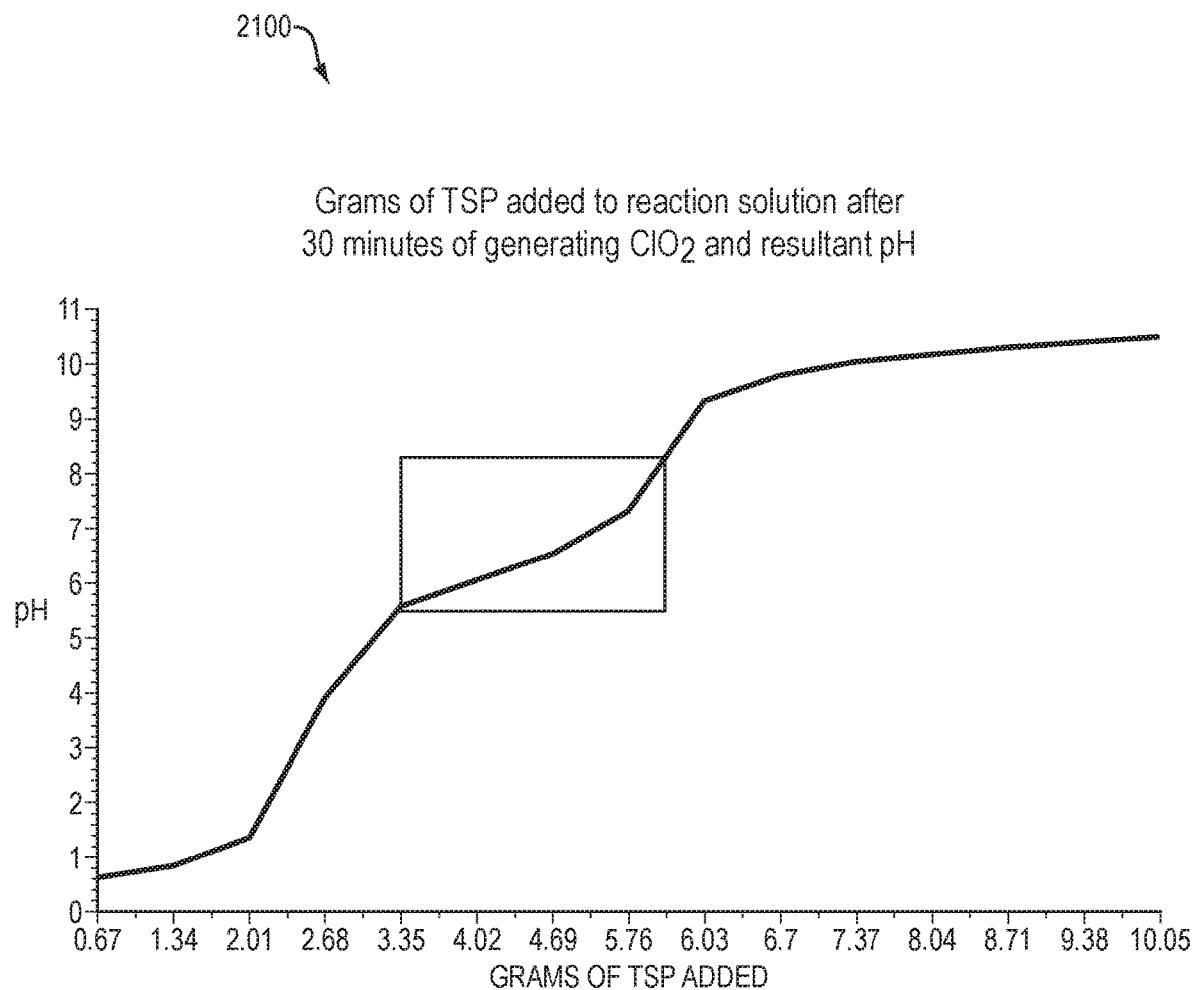
FIG. 21 shows a graph of the pH level for different levels of neutralizer chemical additions described herein.

FIG. 21 shows a graph 2100 of the pH level for tests of the $ClO_2$ generator described herein. Plot 2101 shows amounts of trisodium phosphate were progressively added to the solution remaining after generation of $ClO_2$ as in the experiments shown in FIG. 20, and a range of trisodium phosphate additions was found to produce an acceptable pH level. The device is tunable by using different amounts of chemicals in aqueous solutions in the various chambers described herein to achieve the desired results depending on the requirements of a specific application. In this example, acceptable pH levels of about 5.5 to about 8.3 were achieved by adding approximately 3.35 grams to about 5.76 grams of trisodium phosphate. The curve shows grams of TSP added over time, pH levels of 5.5 to 8.3 are acceptable, corresponding to TSP additions of approximately 3.35 grams to 5.76 grams, shown inside the box.

In describing example embodiments, specific terminology is used for the sake of clarity. For purposes of description, each specific term is intended to at least include all technical and functional equivalents that operate in a similar manner to accomplish a similar purpose. Additionally, in some instances where a particular example embodiment includes system elements, device components or method steps, those elements, components or steps can be replaced with a single element, component or step. Likewise, a single element, component or step can be replaced with a number of elements, components or steps that serve the same purpose. Moreover, while example embodiments have been shown and described with references to particular embodiments thereof, those of ordinary skill in the art will understand that various substitutions and alterations in form and detail can be made therein without departing from the scope of the disclosure. Further still, other aspects, functions and advantages are also within the scope of the disclosure.

What is claimed is:

1. A system for generating a chemical compound, the system comprising:
    a reaction chamber configured to hold a precursor chemical within its internal volume, wherein a surface of the reaction chamber defines a reaction chamber opening providing fluid communication with the internal volume of the reaction chamber;
    a reaction chamber insert configured to be received within the reaction chamber opening;
    an activator chamber configured to hold a activator chemical within its internal volume, wherein a surface of the activator chamber defines an activator chamber opening providing fluid communication with the internal volume of the activator chamber;
    an activator chamber insert configured to be received within the activator chamber opening;
    a quenching and neutralizer chamber configured to hold quenching and neutralizer chemicals within its internal volume, wherein a surface of the quenching and neutralizer chamber defines a quenching and neutralizer chamber opening providing fluid communication with the internal volume of the quenching and neutralizer chamber;
a quenching and neutralizer chamber insert configured to be received within the quenching and neutralizer chamber opening;
a first fluid pathway disposed between the activator chamber opening and the reaction chamber opening;
a second fluid pathway disposed between the quenching and neutralizer chamber opening and the reaction chamber opening; and
a pump configured to selectively pump the activator chemical to the reaction chamber through the first fluid pathway and to pump the quenching and neutralizer chemicals to the reaction chamber through the second fluid pathway.

2. The system of claim 1, wherein the precursor chemical is a precursor chemical in an aqueous solution, the activator chemical is a activator chemical in an aqueous solution, and the quenching and neutralizer chemicals are in an aqueous solution.

3. The system of claim 1, wherein the precursor chemical is an aqueous solution of $NaClO_2$ and the activator chemical is an aqueous solution of HCl, and wherein the precursor chemical and the activator chemical react to form $ClO_2$ gas.

4. The system of claim 3, wherein the reaction chamber opening is further configured to allow $ClO_2$ gas to exit from the reaction chamber.

5. The system of claim 1, wherein the first fluid pathway and the second fluid pathway form a polymeric manifold, and wherein a portion of the polymeric manifold is configured to form a seal with the reaction chamber insert, the activator chamber insert, and the quenching and neutralizer chamber insert.

6. The system of claim 1, wherein a portion of the reaction chamber insert defines a vent configured to allow $ClO_2$ gas to exit from the reaction chamber.

7. The system of claim 1, wherein the reaction chamber is a prefilled chemical cartridge containing an aqueous solution of $NaClO_2$.

8. The system of claim 1, wherein the activator chamber is a prefilled chemical cartridge containing an aqueous solution of HCl.

9. The system of claim 1, further comprising a fluid valve configured to allow the pump to selectively pump the activator chemical and the quenching and neutralizer chemical to the reaction chamber.

10. A disinfecting system comprising:
a prefilled reaction cartridge containing an aqueous solution of $NaClO_2$;
a prefilled activator cartridge containing an aqueous solution of HCl;
a prefilled neutralizer chamber containing an aqueous quenching and neutralizer solution;
a polymeric manifold having a first fluid pathway disposed between the activator cartridge and the reaction cartridge, and a second fluid pathway disposed between the quenching and neutralizer cartridge and the reaction cartridge;
a pump in fluid communication with the activator cartridge and the quenching and neutralizer cartridge and configured to pump the aqueous solution of HCl to the reaction cartridge through the first fluid pathway and to pump the aqueous quenching and neutralizer solution to the reaction cartridge through the second fluid pathway, wherein the aqueous solution of HCl and the aqueous solution of $NaClO_2$ react to form $ClO_2$ gas within the reaction cartridge; and
a fan proximal to an outlet in the reaction cartridge and configured to direct a flow of $ClO_2$ gas from the reaction chamber.

11. The system of claim 10, further comprising a housing configured to receive the prefilled reaction cartridge, the prefilled activator cartridge, and the prefilled quenching and neutralizer cartridge.

12. The system of claim 10, wherein the polymeric manifold is configured to form a seal with the prefilled reaction cartridge, the prefilled activator cartridge, and the prefilled quenching and neutralizer cartridge.

13. The system of claim 10, further comprising a fluid valve configured to allow the pump to selectively pump an aqueous solution of HCl and an aqueous quenching and neutralizer solution to the reaction chamber.

* * * * *